US006638957B1

(12) United States Patent
Jomaa

(10) Patent No.: US 6,638,957 B1
(45) Date of Patent: Oct. 28, 2003

(54) USE OF COMPOUNDS WITH A NITROGEN-OXYGEN HETEROCYCLE

(75) Inventor: Hassan Jomaa, Giessen (DE)

(73) Assignee: Jomaa Pharmaka GmbH, Giessen (DE)

( * ) Notice: Subject to any disclaimer, the term of this patent is extended or adjusted under 35 U.S.C. 154(b) by 0 days.

(21) Appl. No.: 09/980,611

(22) PCT Filed: May 3, 2000

(86) PCT No.: PCT/EP00/03959

§ 371 (c)(1),
(2), (4) Date: Nov. 2, 2001

(87) PCT Pub. No.: WO00/66094

PCT Pub. Date: Nov. 9, 2000

(30) Foreign Application Priority Data

May 3, 1999 (DE) .......................... 199 20 247

(51) Int. Cl.[7] ...................... A61K 31/42; A61K 31/535; A61K 31/66
(52) U.S. Cl. ...................... 514/378; 514/228.8; 514/114
(58) Field of Search .............................. 514/378, 228.8, 514/114

(56) References Cited

U.S. PATENT DOCUMENTS

| 3,418,317 A | 12/1968 | Pifferi et al. |
| 4,209,512 A | 6/1980 | Tomita et al. |
| 4,405,357 A | 9/1983 | Change |

FOREIGN PATENT DOCUMENTS

| JP | 63119476 | * | 5/1988 |
| JP | 07291992 | * | 11/1995 |

OTHER PUBLICATIONS

Simon/Stille, "Antibiokia–Therapie in Klinik und Praxis", 9th edition, 1998, Shattauer Verlag (will follow).
Slawik et al, "Position 5 at the Oxotremorine Skeleton as the Steering Position for Activity at the Muscarinic Receptors", Amstutz et al, Helv. Chim ACTA 1987, 70 (8), pp. 2232–2244.
Slawik et al, "Synthesis of 3–(3oxo–1,2–benzisoxazol–2–yl) propionic acids derivatives", ACTA Pol. Pharm. 1997, 54 (5) 375–379.
Hall et al, "Synthesis and Cytotoxic Action of 3,5–isoxazolidinediones and 2–isoxazolin–5–ones in Murine & Human Tumors", ARCH. Pharm Germany 1997, 330 (3) 67–73.
Hall et al, "Microbial Transformations of Clomazone", Journal of Agricultural and Food Chemistry, vol. 44. No. 1, 1996, pp. 313–319.

* cited by examiner

Primary Examiner—Sreeni Padmanabhan
Assistant Examiner—S. Jiang
(74) Attorney, Agent, or Firm—Harness, Dickey & Pierce, P.L.C.

(57) ABSTRACT

The invention relates to the use of compounds of the general formula (I)

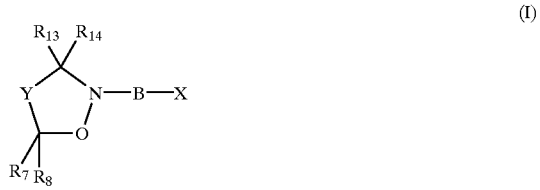

(I)

wherein Y is a $C_{1-3}$-alkenylene group, wherein B is selected from the group, which consists of $C_{1-26}$-alkenylene groups, wherein one C-atom is replaced by an oxygen atom and one C-atom is replaced by a sulphur atom or two C-atoms may be replaced by a S-heterocycle, and wherein X represents the organo phosphorous group.

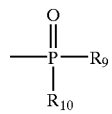

or the amino group

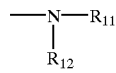

for inhibition of the 1-deoxy-D-xylulose-5-phosphate-(DOXP)-metabolic pathway, use there of as a herbicide and for the preparation of a pharmaceutical preparation as well as a method for the therapeutic and prophylactic treatment of infections in humans and animals, caused by viruses, bacteria, fungi and parasites.

11 Claims, No Drawings

USE OF COMPOUNDS WITH A NITROGEN-OXYGEN HETEROCYCLE

CROSS REFERENCE TO RELATED APPLICATIONS

Applicant claims priority under 35 U.S.C. §119 of German Application No. 199 20 247.8, filed on May 3, 1999. Applicant also a claims priority under 35 U.S.C. §120 of PCT/EP00/03959, filed on May 3, 2000. The international application under PCT article 21(2) was not published in English.

This invention relates to the use of compounds comprising a nitrogen-oxygen heterocycle as an active ingredient and the salts, esters and salts of the esters thereof and for the therapeutic and prophylactic treatment of infections in humans and animals, caused by viruses, bacteria, fungi and parasites, as well as the corresponding treatment and the thereof as a herbicide.

In U.S. Pat. No. 4,209,512 phosphono acid derivatives comprising a nitrogen-oxygen heterocycle are disclosed as insecticides and acaricides.

It has now been found, surprisingly, that compounds according to claim 1 comprising a nitrogen-oxygen heterocycle may be used as an active ingredient for treatment of the above stated infections and as a herbicides. It has been shown by experiments, that the effect of the compounds is based on an inhibition of the 1-deoxy-D-xylulose-5-phosphate-(DOXP) metabolic pathway, which can be proved in micro-organisms and plants, but not for human beings. Accordingly, the compounds according to the present invention show an anti-infectious effect against viruses, bacteria, fungi, uni- and multicellular parasites and as herbicides. Further developments of the invention are defined by the subclaims.

Compounds used according to the present invention correspond to the general formula (I):

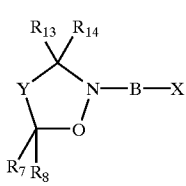

(I)

in which Y is a $C_{1-3}$ alkenylene group, substituted with the substituents $R_1$ and $R_2$ and optionally with the substituents $R_3$ to R6, in which $R_1$ to $R_8$ are the same or different and are selected from the group, which consists of hydrogen, hydroxy, halogen, substituted and unsubstituted alkyl groups, substituted and unsubstituted cycloalkyl ($C_{0-26}$)-alkyl groups, substituted and unsubstituted cycloalkoxy ($C_{0-26}$) alkyl groups, substituted and unsubstituted alkoxy ($C_{0-26}$)-alkyl groups, substituted and unsubstituted amino groups and substituted, unsubstituted thio ($C_{0-26}$)-alkyl groups, substituted and unsubstituted sulfonyl-($C_{0-26}$)-alkyl groups, substituted and unsubstituted sulfinyl-($C_{0-26}$)-alkyl groups and substituted or unsubstituierten acyl radicals, in which each alkyl radical, each alkoxy radical and each acyl radical branched or unbranched and each alkyl radical, each alkoxy radical and each cycloalkyl group may be saturated or unsaturated having one or more double or triple bonds and one or two carbon atoms of the cycloalkyl groups may be replaced by nitrogen, oxygen or sulphur atoms and $R_{13}$ and $R_{14}$ are defined like $R_1$ to $R_8$ or together form an oxo group, wherein X is the organo phosphorous group

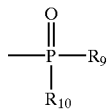

in which $R_9$ and $R_{10}$ are the same or different and are selected from the group, which consists of hydrogen, substituted and unsubstituted ($C_{1-26}$)-alkyl groups, substituted and unsubstituted hydroxy-($C_{1-26}$)-alkyl groups, substituted and unsubstituted cycloalkyl-($C_{0-26}$)-alkyl groups, substituted and unsubstituted acyl, halogen, $OX_9$ or $OX_{10}$, in which each alkyl radical, each alkoxy radical and each acyl radical branched or linear and each alkyl radical, each alkoxy radical and each cycloalkyl group saturated or may be unsaturated having one or more double or triple bonds and one or two carbon atoms of cycloalkyl groups may be replaced by nitrogen, oxygen or sulphur atoms, wherein $X_9$ or $X_{10}$ may be the same or different and are selected from the group, which consists of hydrogen, substituted and unsubstituted ($C_{1-26}$)-alkyl groups, substituted and unsubstituted hydroxy-($C_{1-26}$)-alkyl groups, substituted and unsubstituted cycloalkyl-($C_{0-26}$)-alkyl groups, substituted and unsubstituted acyl, silyl, a cation of an organic and inorganic base, in particular of a metal of main group I, II or III of the periodic system, ammonium, substituted ammonium and ammonium compounds which are derived from ethylenediamine or amino acids, wherein each alkyl radical, each alkoxy radical and each acyl radical branched or unbranched and each alkyl radical, each alkoxy radical and each cycloalkyl group may be saturated or unsaturated having one or more double or triple bonds and one or two carbon atoms of the cycloalkyl groups may be replaced by nitrogen, oxygen or sulphur atoms, or wherein X represents amino group

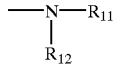

wherein $R_{11}$ and $R_{12}$ are the same or different and are selected from the group, which consists of hydrogen, substituted and unsubstituted alkyl groups, substituted and unsubstituted cyclo-alkyl-($C_{0-26}$)-alkyl groups, substituted and unsubstituted cycloalkoxy-($C_{0-26}$)-alkyl groups, substituted and unsubstituted alkoxy ($C_{0-26}$)-alkyl groups and substituted or unsubstituted acyl radicals, wherein each alkyl radical, each alkoxy radical and each acyl radical branched or unbranched and each alkyl radical, each alkoxy radical and each cycloalkyl group may be saturated or unsaturated having one or more double or triple bonds and one or two carbon atoms of the cycloalkyl groups may be substituted by nitrogen, oxygen or sulphur atoms, wherein B is selected from the group, which consists of substituted and unsubstituted $C_{1-26}$-alkenylene groups, in which one C-atom may be replaced by an oxygen atom and one C atom my be replaced by a sulphur atom or two C-atoms may be replaced by a S-heterocycle and wherein each alkenylene radical may be branched or unbranched and may be saturated or unsaturated having one or more double or triple bonds and may be saturated with one or more hydroxy groups, halogen groups or oxo groups.

Preferably $R_{13}$ and $R_{14}$ together form an oxo group in α-Position to the nitrogen atom.

Y preferably represents a methylene group, which is particularly preferably substituted with two methyl groups.

Compounds, in which B represents ether group (II)

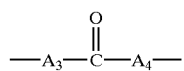
(II)

are advantageous, wherein Al is absent or is a $(C_{1-9})$-alkylene radical, and $A_2$ is absent or selected from the group, which consists of $(C_{1-9})$-alkylene radicals, a sulphur atom and a $(C_{3-8})$-heterocycle, which comprises at least one sulphur atom. It is especially preferred that $A_1$ and $A_2$ each represent a methylene group.

Also compounds, in which B represents a keto group (III)

$$—A_3—\overset{\overset{O}{\|}}{C}—A_4—$$
(III)

are advantageous, wherein $A_3$ and $A_4$, out of which one or both may be absent, are the same or different, may be selected from the group, which consists of $(C_{1-9})$-alkylene radicals, wherein all the $(C_{1-9})$-alkylene radicals may be branched or unbranched, may have one ore more double bonds or may be substituted with a hydroxyl group or a halogen group. It is particularly preferred that $A_3$ is absent and $A_4$ represents a methylene or an ethylene group.

Preferably B furthermore is a 2-hydroxypropylene group.

$R_9$ and $R_{10}$ preferably represent $OX_9$ and $OX_{10}$, wherein $X_9$ and $X_{10}$ are the same or different and are selected from the group, which consists of a metal of the first, second or third main group of the periodic system, in particular sodium and potassium, and methyl, ethyl.

Examples for individual compounds are listed in the following:

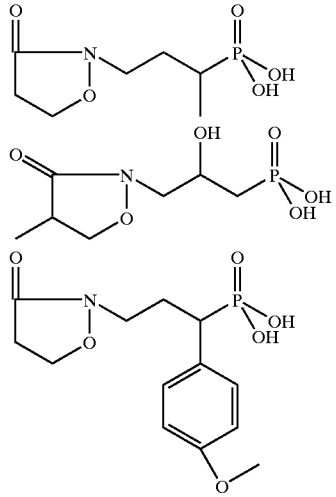

-continued

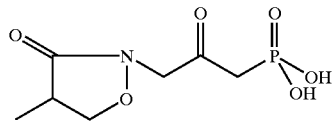

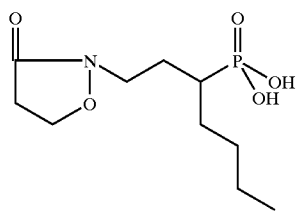

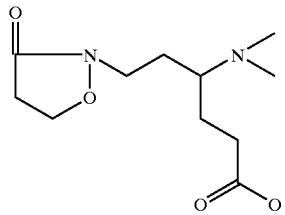

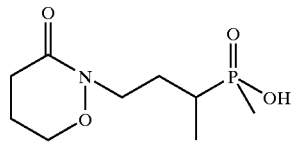

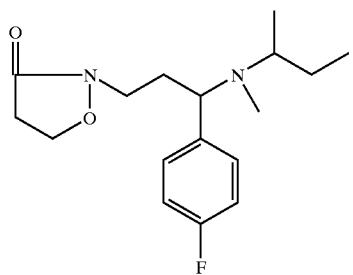

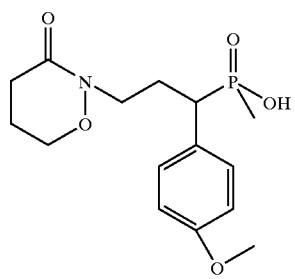

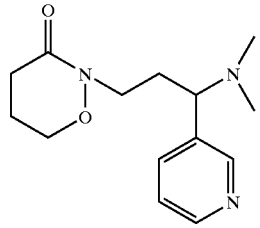

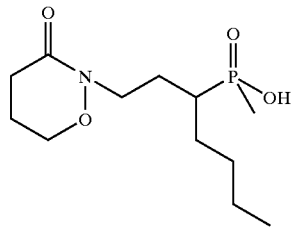

-continued
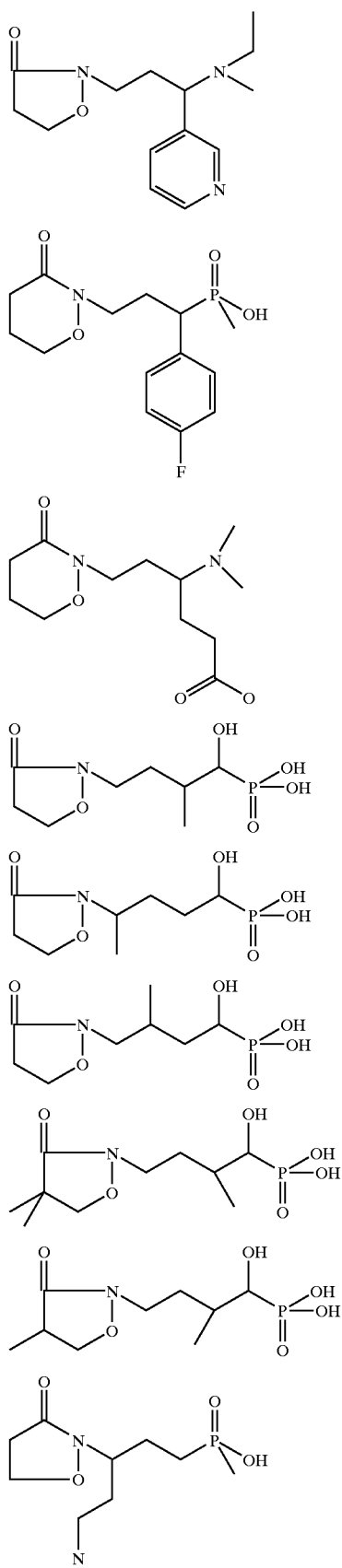
-continued
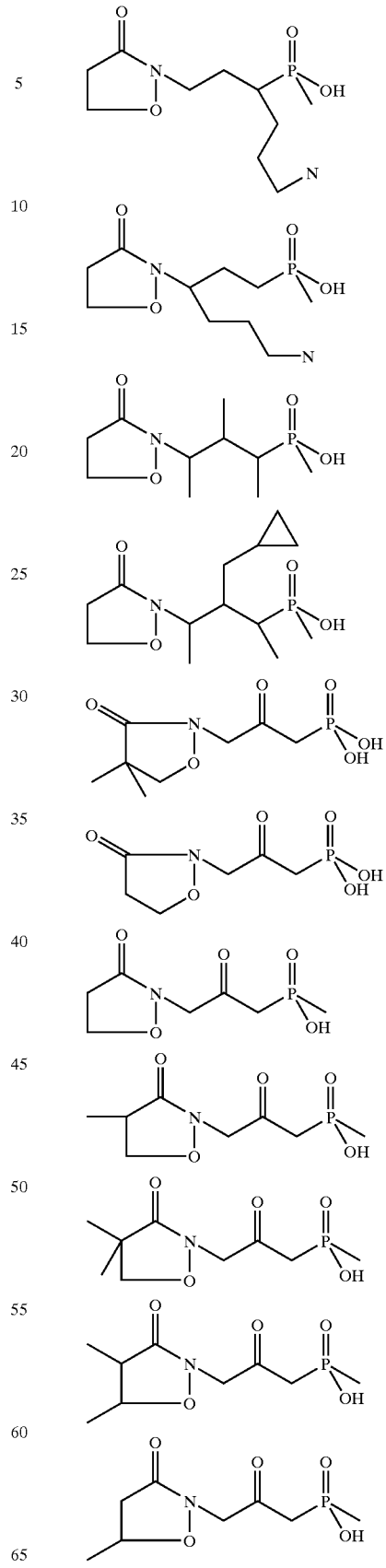

-continued

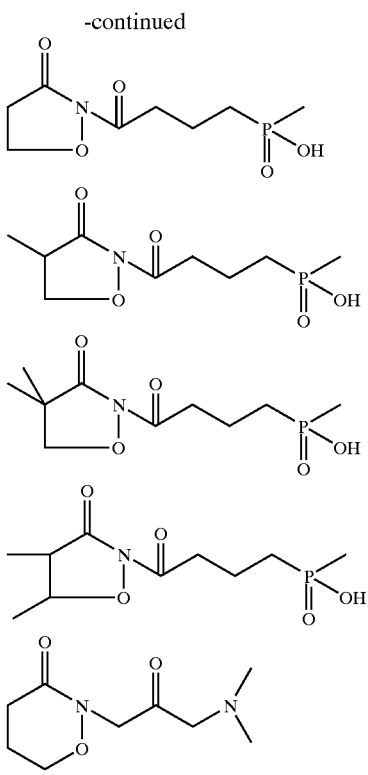

The following compounds are in particular preferred:

1)
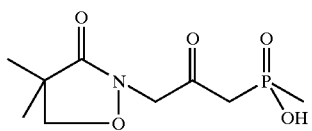

2)
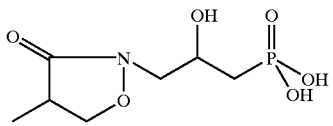

3)
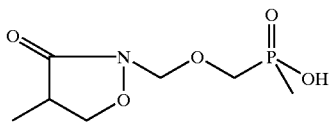

4)
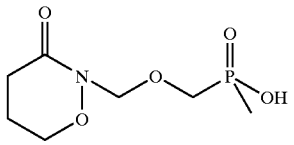

5)
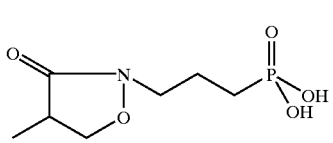

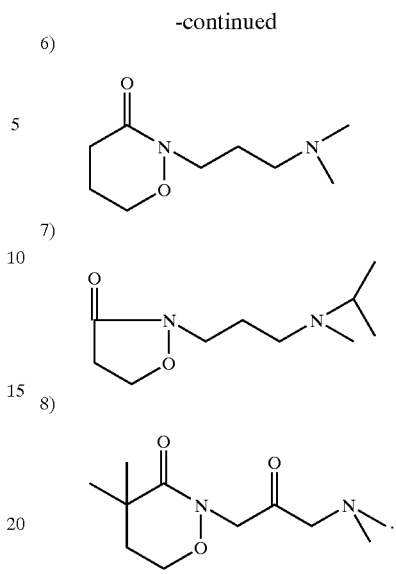

Special features of the above definitions and suitable examples thereof are stated below:

"Acyl" is a substituent which originates from an acid, such as from an organic carboxylic acid, carbonic acid, carbamic acid or the thioacid or imidic acid corresponding to the individual above-stated acids, or from an organic sulfonic acid, wherein these acids may in each case comprise aliphatic, aromatic and/or heterocyclic groups in the molecule, as well as carbamoyl or carbamimidoyl.

Suitable examples of these acyl groups are stated below.

Aliphatic acyl groups are deemed to comprise acyl radicals originating from an aliphatic acid, such groups including the following:

alkanoyl (for example formyl, acetyl, propionyl, butyryl, isobutyryl, valeryl, isovaleryl, pivaloyl etc.);

alkenoyl (for example acryloyl, methacryloyl, crotonoyl etc.); alkylthioalkanoyl (for example methylthioacetyl, ethylthioacetyl etc.); alkanesulfonyl (for example mesyl, ethanesulfonyl, propanesulfonyl etc.); alkoxycarbonyl (for example methoxycarbonyl, ethoxycarbonyl, propoxycarbonyl, isopropoxycarbonyl, butoxycarbonyl, isobutoxycarbonyl etc.); alkylcarbamoyl (for example methylcarbamoyl etc.); (N-alkyl)thiocarbamoyl (for example (N-methyl)thiocarbamoyl etc.); alkylcarbamimidoyl (for example methylcarbamimidoyl etc.); oxalo;

alkoxalyl (for example methoxalyl, ethoxalyl, propoxalyl etc.).

In the above examples of aliphatic acyl groups, the aliphatic hydrocarbon moiety, in particular the alkyl group or alkane radical, may optionally comprise one or more suitable substituents, such as amino, halogen (for example fluorine, chlorine, bromine etc.), hydroxy, hydroxyimino, carboxy, alkoxy (for example methoxy, ethoxy, propoxy etc.), alkoxycarbonyl, acylamino (for example benzyloxycarbonylamino etc.), acyloxy (for example acetoxy, benzyloxy etc.) and the like; preferred aliphatic acyl radicals having such substituents which may be mentioned are alkanoyls substituted, for example, with amino, carboxy, amino and carboxy, halogen, acylamino or the like.

Aromatic acyl radicals are deemed to comprise those acyl radical which originate from an acid with a substituted or unsubstituted aryl group, wherein the aryl group may comprise phenyl, toluyl, xylyl, naphthyl and the like; suitable examples are stated below: aroyl (for example benzoyl, toluoyl, xyloyl, naphthoyl, phthaloyl etc.); aralkanoyl (for example phenylacetyl etc.); aralkenoyl (for example cinnamoyl etc.); aryloxyalkanoyl (for example phenoxyacetyl etc.); arylthioalkanoyl (for example phenylthioacetyl etc.); arylaminoalkanoyl (for example N-phenylglycyl etc.); arenesulfonyl (for example benzenesulfonyl, tosyl or toluenesulfonyl, naphthalenesulfonyl etc.); aryloxycarbonyl (for example phenoxycarbonyl, naphthyloxycarbonyl etc.); aralkoxycarbonyl (for example benzyloxycarbonyl etc.); arylcarbamoyl (for example phenylcarbamoyl, naphthylcarbamoyl etc.); arylglyoxyloyl (for example phenylglyoxyloyl etc.).

In the above examples of acyl radicals, the aromatic hydrocarbon moiety (in particular the aryl radical) and/or the aliphatic hydrocarbon moiety (in particular the alkane radical) may optionally comprise one or more suitable substituents, such as those which have already been stated as suitable substituents for the alkyl group or the alkane radical. Aromatic acyl radicals having particular substituents which may in particular be mentioned and constitute examples of preferred aromatic acyl radicals are aroyl substituted with halogen and hydroxy or with halogen and acyloxy, and aralkanoyl substituted with hydroxy, hydroxyimino, dihaloalkanoyloxyimino, together with arylthiocarbamoyl (for example phenylthiocarbamoyl etc.); arylcarbamimidoyl (for example phenylcarbamimidoyl etc.).

A heterocyclic acyl radical is taken to mean an acyl radical which originates from an acid with a heterocyclic group; these include:

heterocyclic carbonyl, in which the heterocyclic radical is an aromatic or aliphatic 5- to 6- membered heterocycle with at least one heteroatom from the group comprising nitrogen, oxygen and sulphur (for example thiophenyl, furoyl, pyrrolocarbonyl, nicotinoyl etc.);

alkanoyl heterocycle, in which the heterocyclic radical is 5- to 6-membered and comprises at least one heteroatom from the group comprising nitrogen, oxygen and sulphur (for example thiophenylacetyl, furylacetyl, imidazolylpropionyl, tetrazolylacetyl, 2-(2-amino-4-thiazolyl)-2-methoxyiminoacetyl etc.) and the like.

In the above examples of heterocyclic acyl radicals, the heterocycle and/or the aliphatic hydrocarbon moiety may optionally comprise one or more suitable substituents, such as those as have been stated to be suitable for alkyl and alkane groups.

"Alkyl", unless defined otherwise, is a straight- or branched-chain alkyl radical having up to 26 carbon atoms, such as methyl, ethyl, propyl, isopropyl, butyl, isobutyl, tert.-butyl, pentyl, hexyl and the like. It may be substituted e.g. by hydroxy, amino, halogen (e.g. fluorine, bromine, chlorine), oxo radicals and alkoxy radicals, such as methoxy, ethoxy radicals.

"Alkoxy radicals", unless defined otherwise, is a straight- or branched-chain alkyl radical (having up to 26 carbon atoms, such as methoxy, ethoxy radicals etc. It may be substituted e.g. by hydroxy, amino, halogen, oxo groups and alkoxy radicals, such as methoxy, ethoxy radicals.

"Alkoxy-($C_{0-26}$)-alkyl" groups are alkoxy radicals, which can also be bonded to the basic structure via an alkyl radical. The alkyl and alkoxy groups are as defined above.

"Cycloalkyl-($C_{0-26}$)-alkyl radicals are cyclic compounds having 3 to 8 carbon atoms, unless defined otherwise, which are bonded to the basic structure directly or via an alkylene radical. The alkylene radical can be branched, unbranched and saturated or unsaturated having double bonds. Possible substituents of the cycloalkyl radical are, inter alia, alkoxy radicals, alkyl radicals, hydroxyl radicals, halogen radicals, amino radicals, oxo radicals. The cycloalkyl groups can also be aromatic with the corresponding number of double bonds, i.e. aryl-($C_{0-26}$)-alkyl radicals (e.g. phenyl, pyridyl, naphthyl etc). The aromatic cyclic compounds in particular can furthermore contain substituents, such as nitro groups and $CF_3$ and phenyl radicals.

"Cycloalkoxy-($C_{0-26}$)-alkyl radicals are cyclic compounds having 3 to 8 carbon atoms, unless defined otherwise, which are bonded to the basic structure via an oxygen directly or via an alkylene radical. The alkylene radical can be branched, unbranched and saturated or unsaturated "with double bonds. Possible substituents of the cycloalkyl radical are, inter alia, alkoxy radicals, (including alkylenedioxy radicals, such as methylenedioxy), alkyl radicals, hydroxyl radicals, halogen radicals, amino radicals, oxo radicals. The cycloalkyl groups can also be polycyclic radicals and aromatic with the corresponding number of double bonds (e.g. phenoxy, pyridoxy, naphthoxy etc). The aromatic cyclic compounds in particular can furthermore contain substituents, such as nitro groups and $CF_3$ and phenyl radicals.

"Amino radicals" can be substituted, for example by the alkyl radicals or cycloalkyl-($C_{0-26}$)-alkyl radicals as defined above.

"Amino-($C_{0-26}$)-alkyl groups" are amino radicals, which can also be bonded to the basic structure via an alkyl radical. Alkyl and amino groups are defined as above.

"Silyl radicals" may be substituted for example with the above defined alkyl radicals or cycloalkyl ($C_{0-26}$)-alkyl radicals.

"Thio($C_{0-26}$)-alkyl groups", "Sulfonyl-($C_{0-26}$)-alkyl groups" and "Sulfinyl-($C_{0-26}$)-alkyl groups" may be substituted for example with the above defined alkyl radicals or cycloalkyl-($C_{0-26}$)alkyl radicals. The ($C_{0-26}$)-alkyl groups are linear or branched alkylene radicals, such as methylene, ethylene, propylene, isopropylene, butylene, isobutylene, tert.-butylene, pentylene, hexylene and the like. They may comprise double or triple bonds and may be substituted for example with hydroxy, amino, halogen (e.g. fluorine, bromine, chlorine), oxo radicals and alkoxy radicals, such as methoxy, ethoxy radicals.

The radicals $X_9$ and $X_{10}$ may preferably be selected such that esters are formed on the phosphino group. Suitable examples of such esters of the formula (I) include alkyl esters (for example; methyl esters, ethyl esters, propyl esters, isopropyl esters, butyl esters, isobutyl esters, hexyl esters etc.); aralkyl esters (benzyl esters, phenylethyl esters, benzhydryl esters, trityl esters etc.); aryl esters (for example phenyl esters, tolyl esters, naphthyl esters etc.); aroylalkyl esters (for example phenacyl esters etc); and silyl esters (for example of trialkylhalosilyl, dialkyldihalosilyl, alkyltrihalosilyl, dialkylarylhalosilyl, trialkoxyhalosilyl, dialkylaralkylhalosilyl, dialkoxydihalosilyl, trialkoxyhalosilyl etc.) and the like.

In the above ester, the alkane and/or arene moiety may optionally comprise at least one suitable substituent, such as halogen, alkoxy, hydroxy, nitro or the like.

$X_9$ and $X_{10}$ are preferably a metal of main group I, II or III of the periodic system, ammonium, substituted ammonium or ammonium compounds which are derived from ethylenediamine or amino acids. In other words, the salt compounds of the organophosphorus compounds are formed with organic or inorganic bases (for example sodium salt, potassium salt, calcium salt, aluminium salt, amoniun salt, magnesium salt, triethylamine salt, ethanolamine salt, dicyclohexylamine salt, ethylenediamine salt, N,N'- dibenzylethylenediamine salt etc.) as are salts with amino acids (for example arginine salt, aspartic acid salt, glutamic acid salt etc.) and the like.

The compounds of the formula (I) according to the invention permit the occurrence of spatial isomers, for example for double bond-containing or chiral groups $R_1$ to $R_4$, $A_1$ to $A_4$. The use according to the invention of the compounds includes all spatial isomers, both as pure substances and in the form of mixtures thereof.

The compounds are in particular suitable for the therapeutic and prophylactic treatment of human and animal infections which are caused by viruses, bacteria, uni- and multicellular parasites and fungi.

The compounds are active against unicellular parasites (protozoa), in particular against the causative organisms of malaria and sleeping sickness and of Chagas' disease, toxoplasmosis, amoebic dysentery, leishmaniases, trichomoniasis, pneumocystosis, balantidiasis, cryptosporidiosis, sarcocytosis, acanthamoebosis, naeglerosis, coccidiosis, giardiasis and lambliasis.

They are accordingly in particular suitable for the prophylactic treatment of malaria and of sleeping sickness and of Chagas' disease, of toxoplasmosis, amoebic dysentery, leishmaniases trichomoniasis, pneumocystosis, balantidiasis, cryptosporidiosis, sarcocytosis, acanthamoebosis, naeglerosis; coccidiosis, giardiasis and lambliasis.

The active substances according to the invention may in particular be used against the following bacteria:

bacteria of the family Propionibacteriaceae, in particular of the genus Propionibacterium, in particular the species *Propionibacterium acnes*, bacteria of the family Actinomycetaceae, in particular of the genus Actinomyces, bacteria of the genus Corynebacterium, in particular the species *Corynebacterium diphtheriae* and *Corynebacterium pseudotuberculosis*, bacteria of the family Mycobacteriaceae, of the genus Mycobacterium, in particular the species *Mycobacterium leprae, Mycobacterium tuberculosis, Mycobacterium bovis* and *Mycobacterium avium*, bacteria of the family Chlamydiaceae, in particular the species *Chiamydia trachomatis* and *Chlamydia psittaci*, bacteria of the genus Listeria, in particular the species *Listeria monocytogenes*, bacteria of the species *Erysipelthrix rhusiopathiae*, bacteria of the genus Clostridium, bacteria of the genus Yersinia, the species *Yersinia pestis, Yersinia pseudotuberculosis, Yersinia enterocolitica* and *Yersinia ruckeri*, bacteria of the family Mycoplasmataceae, of the genera Mycoplasma and Ureaplasma, in particular the species *Mycoplasma pneumoniae*, bacteria of the genus Brucella, bacteria of the genus Bordetella, bacteria of the genus Campylobacter, in particular the species Campylobacterjejuni, *Campylobacter coli* and *Campylobacter fetus*, bacteria of the genus Helicobacter, in particular the species *Helicobacter pylori*, bacteria of the families Spirochaetaceae and Leptospiraceae, in particular the genera Treponema, Borrelia and Leptospira, in particular *Borrelia burgdorferi,* bacteria of the genus Actinobacillus, bacteria of the family Legionellaceae, of the genus Legionella, bacteria of the family Rickettsiaceae and the family Bartonellaceae, bacteria of the genera Nocardia and Rhodococcus and bacteria of the genus Dermatophilus.

Organophosphorus compounds and the derivatives thereof are consequently suitable for treating diphtheria, acne vulgaris, listerioses, swine erysipelas in animals, gas gangrene in humans and animals, malignant oedema in humans and animals, tuberculosis in humans and animals, leprosy and further mycobacterioses in humans and animals, paratuberculosis in animals, plague, mesenterial lymphadenitis and pseudotuberculosis in humans and animals, cholera, legionnaires' disease, borreliosis in humans and animals, leptospiroses in humans and animals, syphilis, Campylobacter enteritis infections in humans and animals, Moraxella keratoconjunctivitis and serositis in animals, brucellosis of animals and humans, anthrax in humans and animals, actinomycosis in humans and animals, streptotrichoses, psittacoisis/orthithosis in animals, Q fever, ehrlichiosis.

Use is furthermore effective in the eradication of Helicobacter in ulcers of the gastrointestinal tract.

Combinations with another antibiotic may also be used to treat the above-stated diseases. Isoniazid, rifampicin, ethambutol, pyrazinamide, streptomycin, protionamide and dapsone are in particular suitable for combination preparations with other anti-infective agents for the treatment of tuberculosis.

The active substances according to the invention are furthermore usable in infections with the following viruses:

Parvoviridae: parvo viruses, dependo viruses, densoviruses, Adenoviridae: adeno viruses, mastadeno viruses, aviadeno viruses, Papovaviridae, papovaviruses, in particular papillomaviruses ("wart" viruses), polyomaviruses, in particular JC virus, BK virus and miopapovaviruses, Herpesviridae: all herpesviruses, in particular herpes simplex viruses, varicellazoster viruses, human cytomegalovirus, Epstein-Barr viruses, all human herpesviruses, human herpesvirus 6, human herpesvirus 7, human herpesvirus 8, Poxiviridae: poxviruses, orthopoxviruses, parapoxviruses, miolluscum contagiosum virus, aviviruses, capriviruses, leporipoxviruses all primarily hepatotropic viruses, hepatitisviruses: hepatitis A viruses, hepatitis B viruses hepatitis C viruses, hepatitis D viruses, hepatitis E viruses, hepatitis F viruses, hepatitis G viruses, Hepadnaviruses: all hepatitisviruses, hepatitis B virus, hepatitis D viruses, Picornaviridae: picornaviruses, all entero viruses, all polioviruses, all coxsackie-viruses, all echoviruses, all rhinoviruses, hepatitis A virus, aphthoviruses, Calciviridae'.hepatitis E viruses, Reoviridae: reoviruses, orbiviruses, rotaviruses, Togaviridae: togaviruses, alphaviruses, rubiviruses, pestiviruses, rubellavirus, Flaviviridae: flaviviruses, FSME virus, hepatitis C virus, Orthomyxoviridae: all influenza viruses, Paramyxoviridae: paramyxo viruses, morbillivirus, pneumo virus, measles virus, mumps virus, Rhabdoviridae'.rhobdo viruses, rabies virus, lyssavirus, vascular stomatitisvirus, Coronaviridae: coronaviruses, Bunyaviridae: bunyaviruses, nairo virus, phlebo virus, uukuvirus, hantavirus, hantaan virus, Arenaviridae: arenaviruses, lymphocytic choriomeningitis virus, Retroviridae: retro viruses, all HTL viruses, human T-cell leukaemia virus, oncornaviruses, spumaviruses, lentiviruses, all HI viruses, Filoviridae: Marburg and Ebola virus, slow-virus infections, prions, onco viruses and leukaemia viruses.

The organophosphorus compounds used according to the invention are consequently suitable for combating the following viral infections:

eradication of papillomaviruses to prevent tumours, in particular tumours of the reproductive organs caused by papillomaviruses in humans, eradication of JC viruses and BK viruses, eradication of herpesviruses, eradication of human herpesvirus 8 to treat Kaposi's sarcoma, eradication of cytomegaloviruses before transplantations, eradication of Epstein-Barr viruses before transplantation and to prevent tumours associated with Epstein-Barr viruses, eradication of hepatitis viruses to treat chronic liver disease and to prevent liver tumours and cirrhosis of the liver, eradication of coxsackieviruses in cardiomyopathy, eradication of coxsackieviruses in diabetes mellitus patients, eradication of immunodeficiency viruses in humans land animals, treatment of accompanying infections in AIDS patients, treatment of respiaratorytract inflammation of viral causation (laryngeal papilloma, hyperplasia, rhinitis, pharyngitis, bronchitis, pneumonia), of the sensory organs (keratoconjunctivitis), of the nervous system (poliomyelitis, meningoencephalitis, encephalitis, subacute sclerosing panencephalitis, SSPE, progressive multifocal leukoencephalopathy, lymphocytic choriomeningitis), of the gastrointestinal tract (stomatitis, gingivostomatitis, oesophagitis, gastritis, gastroenteritis, diarrhoea), of the liver and gall system (hepatitis, cholangitis, hepatocellular carcinoma), of the lymphatic tissue (mononucleosis, lymphadenitis), of the haemopoietic system, of the reproductive organs (mumps orchitis), of the skin (warts, dermatitis, herpes labialis, herpes febrilis, z herpes zoster, shingles), of the mucous membranes (papillomas, conjunctival papillomas, hyperplasia, dysplasia), of the cardiovascular system (arteriitis, myocarditis, endocarditis, pericarditiis), of the kidney/urinary system, of the reproductive organs (anogenital lesions, warts, genital warts, sharp condylomas, dysplasia, papillomas, cervical dysplasia, condyloma acuminatum, epidermodysplasia verruciformis), of the locomotory organs (myositis, myalgia), treatment of foot-and-mouth disease in cloven-hoofed animals, of Colorado tick fever, Dengue syndrome, of haemorrhagic fever, of early summer meningoencephalitis (FSME) and of yellow fever.

The compounds according to the invention, which generally include for this purpose pharmaceutically acceptable salts, amides, esters, a salt of such an ester or also compounds which, on administration, provide the compounds used according to the invention as metabolites or breakdown products, also called "prodrugs", may be formulated for administration in any suitable manner analogous to known agents having an anti-infective action (mixed with a non-toxic, pharmaceutically acceptable excipient).

Pharmaceutically acceptable salts of the compounds include salts which the compounds of the formulae (I) used according to the invention form in their protonated form as an ammonium salt of inorganic or organic acids, such as hydrochloric acid, sulphuric acid, citric acid, maleic acid, fumaric acid, tartaric acid, p-toluenesulfonic acid.

The salts, such as sodium salt, potassium salt, calcium salt, ammonium salt, ethanolamine isalt, triethylamine salt, dicyclohexylamine salt and salts of an amino acid such as arginine isalt, aspartic acid salt, glutamic acid salt, are also particularly pharmaceutically suitable.

The activity of the substances is determined using a test system. This system is based upon in vitro measurement of the inhibition of growth of bacteria, parasites, viruses, fungi or plants. Test methods known to the person skilled in the art are in part used for this purpose.

For example, antimalarial activity is determined by measuring the inhibition of the growth of malaria parasites in blood cultures.

Antibacterial activity is determined on the basis of measuring the inhibition of bacterial growth on nutrient media and in liquid cultures. Antiviral activity is determined on the basis of the formation of viral elements in cell cultures. Fungicidal activity is determined on the basis of measuring the inhibition of fiingal growth on nutrient media and in liquid cultures Some of the micro-organisms which are to be investigated may only be investigated in animal models. In this case, we will then use the appropriate models.

Substances which exhibit activity in in vitro measurement systems are then further investigated in in vivo models. The antiparasitic, antiviral, fungicidal or antibacterial activity is further evaluated in the appropriate animal models.

The pharmaceutically active agents may be prepared in dosage units in the form of pharmaceutical preparations. This means that the preparation is in the form of individual components, for example tablets, coated tablets, capsules, pills, suppositories and ampoules, the active substance content of which corresponds to a fraction or multiple of an individual dose. The dosage units may contain, for example 1, 2, 3 or 4 individual doses or ½, ⅓ or ¼ of an individual dose. An individual dose preferably contains the quantity of active substance which is adiministered at one time and usually corresponds to a whole, half, third or quarter of a daily dose.

Non-toxic, inert, pharmaceutically suitable excipients should be taken to mean solid, semisolid or liquid diluents, fillers and formulation auxiliaries of all kinds.

Preferred pharmaceutical preparations which may be mentioned are tablets, coated tablets, capsules, pills, granules, suppositories, solutions, suspensions and emulsions, pastes, ointments, gels, creams, lotions, powders and sprays. Tablets, coated tablets, capsules, pills and granules may contains the active substances together with conventional excipients, such as (a) fillers and extenders, for example starches, lactose, cane sugar, glucose, mannitol and silica, (b) binders, for example carboxymethylcellulose, alginates, gelatine, polyvinylpyrrolidone, (c) humectants, for example glycerol, (d) suspending agents, for example agar-agar, calcium carbonate and sodium carbonate, (e) dissolution retardants, for example paraffin and (f) resorption accelerators, for example quaternary ammonium compounds, (g) wetting agents, for example acetyl alcohol, glycerol monostearate, (h) adsorbents, for example kaolin and bentonite and (i) lubricants, for example talcum, calcium and magnesium stearate and solid polyethylene glycols or mixtures of the substances stated in (a) to (i).

The tablets, coated tablets, capsules, pills and granules may be provided with conventional coatings and shells optionally containing opacifying agents and may also he composed such that they release the active substances only with a delay or preferably in a particular part of the intestinal tract, wherein polymeric substances and waxes may, for example, be used as the matrices.

The active substance or substances, optionally together with one or more of the above-stated excipients, may also be present in microencapsulated form.

In addition to the active substance or substances, suppositories may contain conventional water-soluble or water-insoluble excipients, for example polyethylene glycols, fats, for example cocoa butter and higher esters (for example $C_{14}$ alcohol with $C_{16}$ fatty acid) or mixtures of these substances.

In addition to the active substance or substances, ointments, pastes, creams and gels may contain conventional excipients, for example animal and vegetable fats, waxes, paraffins, starch, gum tragacanth, cellulose derivatives, polyethylene glycols, silicones, bentonites, silica, talcum and zinc oxide or mixtures of these substances.

In addition to the active substance or substances, powders and sprays may contain conventional excipients, for example lactose, talcum, silica, aluminium hydroxide, calcium silicate and polyamide powder or mixtures of these substances. Sprays may additionally contain conventional propellants, for example chlorofluorocarbons.

In addition to the active substance or substances, solutions and emulsions may contain conventional excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, peanut oil, corn oil, olive oil, castor oil and sesame oil, glycerol, glycerol formal, tetrahydrofurfuryl alcohol, polyethylene glycols and sorbitan fatty acid esters or mixtures of these substances.

For parenteral administration, the solutions and emulsions may also be present in sterile, isotonic form.

In addition to the active substance or substances, suspensions may contain conventional excipients, such as liquid diluents, for example water, ethyl alcohol, propylene glycol, suspending agents, for example ethoxylated isostearyl alcohols, polyoxyethylene sorbitol and sorbitan esters, microcrystalline cellulose, aluminium metahydroxide, bentonite, agar-agar and gum tragacanth or mixtures of these substances.

The stated formulations may also contain colorants, preservatives and odour- or flavour- enhancing additives, for example peppermint oil and eucalyptus oil, and sweeteners, for example saccharin.

The active substances of the formulae (I) should preferably be present in the pharmaceutical preparations listed above in a concentration of approx. 0.1 to 99.5 wt. %, preferably from approx. 0.5 to 95 wt. %, of the complete mixture.

Apart from the compounds of the formulae (I), the pharmaceutical preparations may also contain further pharmaceutical active substances.

The coimpounds may be used together with hitherto described substances having antibacterial, antiviral, antimycotic and antiparasitic properties. Such substances in particular include cornpounds which have already been used in therapeutic applications or are still used. Substances which are suitable for this purpose are in particular those listed in the Red List or in Simorn/Stille, *Antibiokia-Therapie in Klinik und Praxis*, 9th edition, 1998, Schattauer Verlag, or on the Internet at http://www.customs.treas.gov/imp-exp/rulings/harmoniz/hrm 129.html. The derivatives may in particular be present with penicillins, benzylpenicillin (penicillin G), phenoxypenicillins, isoxazolylpenicillins, aminopenicillins, ampicillin, amoxicillin, bacampicillin, carboxypenicillin, ticarcillin, temnocillin, acylaminopenicillins, azlocillin, mezlocillin, piperacillin, atialcilliri mecillinam, cephalosporins, cefazolin group, cefuroxime group, cefoxitin group, cefoxitin, cefotetan, cefinetazole, latamoxef, flomoxef, cefotaxime group, cefozidime, ceflazidime group, ceftazidime, cefpirome, cefepime, conventional cephalosporins, cefsulodin, cefoperazone, oral cephalosporins of the cephalexin group, loracarbef, cefprozil, new broad-spectrum oral cephalosporins, cefixime, cefpodoxime-proxetil, cefttroxirne-axetil, cefetamet, cefotiam-hexetil, cefdinir, ceftibuten, other β-lactam antibiotics, carbapenem, imipenem/cilastatin, meropenem, biapenem, aztreonam, β-lactamase inhibitors, clavulanic acid/arnoxicillin, clavulanic acid/ticarcillin, sulbactam/ampicillin, tazobactam/piperacillin, tetracyclines, oxytetracycline, rolitetracycline, doxycycline, minocycline, chloramphenicol, aminoglycosides, gentamicin, tobramycin, netilmicin, amikacin, spectinomycin, macrolides, erythromycin, clarithromycin, roxithromycin, azithromycin, dirithromycin, spiramycin, josamycin, lincosamides, clindamycin, fusidic acid, glycopeptide antibiotics, vancomycin, teicoplanin, pristinamycin derivatives, fosfomycin, antimicrobial folic acid antagonists, sulfonamides, co-trimoxazole, trimethoprim, other diaminopyrimidine-sulfonamide combinations, nitrofurans, nitrofuirantoin, nitrofuirazone, gyrase inhibitors (quinolones), norfloxacin, ciprofloxacin, ofloxacin, sparfloxacin, enoxacin, fleroxacin,-pefloxacin, lomefloxacin, Bay Y3118, nitroimidazoles, antimycobacterial agents, isoniazid, rifampicin, rifabutin, ethambutol, pyrazinamide, streptomycin, capreomycin, prothionamide, terizidone, dapsone, clofazimine, topical antibiotics, bacitracin, tyrothricin, polymyxins, neomycin, kanamycin, parornomycin, mupirocin, antiviral agents, acyclovir, ganciclovir, azidothymidine, didanosine, zalcitabine, thiacytidine, stavudine, ribavirin, idoxuridine, trifluridine, foscamet, amantadine, interferons, tibol derivatives, proteinase inhibitors, antimycotics, polyenes, amphotericin B, nystatin, natamycin, azoles, azoles for septic therapy, miconazole, ketoconazole, itraconazole, fluconazole, UK-109.496, azoles for topical use, clotrimazole, econazole, isoconazole, oxiconazole, bifonazole, flucytosine, griseofulvin, ciclopirox olamine, tolnafnate, naftifine, terbinafine, amorolfine, anthraquinones, betulinic acid, semianthraquinones, xanthones, naphthoquinones, arylamino alcohols, quinine, quinidines, mefloquine, halofantrine, chloroquine, amodiaquine, acridine, benzonaphthyridine, mepacrine, pyronaridine, dapsone, sulfonamides, sulfadoxine, sulfalenes, trimethoprim, proguanil, chiorproguanil, diamninopyrirnidines, pyrimethamine, primaquine, aminoquinolines, WR 238,605, tetracycline, doxycycline, clindamycin, norfloxacin, ciprofloxacin, ofloxacin, artemisinin, dihydroartemisinin, 10b arternether, arteether, atresunate, atovaquone, suramin, melarsoprol, nifurtimox, stibogluconate sodium, pentamidine, amphotericin B, metronidazole, clioquinol, mebendazole, niclosamide, praziquantel, pyrantel, tiabenzazole, diethylcarbamazine, ivermectin, bithionol, oxamniquine, metrifonate, piperazine, embonate.

The compounds according to the present invention may furthermore be present in the pharmaceutical preparations in combination with sulfonamide, sulfadoxine, artemisinin, atovaquone, quinine, chloroquine, hydroxychioroquine, mefloquine, halofantrine, pyrimethamine, armeesin, tetracyclines, doxycycline, proguanil, metronidazole, praziquantel, niclosamide, mebendazole, pyrantel, tiabendazole, diethylcarbazine, piperazine, pyrivinium, metrifonate, oxamniquine, bithionol or suramin or two or more of these substances.

The above-stated pharmaceutical preparations are produced in the conventional manner using known methods, for example by mixing the active substance or substances with the excipient or excipients.

The stated preparations may be administered to humans and animals orally, rectally, parenterally (intravenously, intramuscularly, subcutaneously), intracistemally, intravaginally, intraperitoneally, topically (powders, ointments, drops) and for the treatment of infections in cavities, ibody cavities. Suitable preparations which may be considered are solutions for injections, solutions and suspensions for oral therapy, gels, infusion formulations, emulsions, ointments or drops. Topical treatment may be performed using ophthalmological and dermatological forrnulations, silver and other salts, ear drops, eye ointments, powders or solutions. Administration to animals may also be achieved via the feed or drinking water in suitable formulations. Gels, pulverulent formulations, powders, tablets, controlled-release tablets, premixes, concentrates, granules, pellets, tablets, boli, capsules, aerosols, sprays, inhalation formulations may also be used in humans and animals. The compounds used according to the invention may also be incorporated into other supports, such as for example plastics (plastic chains for topical treatment), collagen or bone cement.

It has in general proved advantageous in both human and veterinary medicine to administer the aQctive substances of the formulae (I) in total quantities of approx. 0.05 to approx. 600, preferably of 0.5 to 200 mg/kg body weight per 24 hours, optionally in the form of two or more individual doses in order to achieve the desired results. An individual dose preferably contains the active substance or substances in quantities of approx. 1 to approx. 200, in particular of 1 to 60 mg/kg body weight. It may, however, be necessary to deviate from the stated dosages, in particular as a function of the nature and body weight of the patient to be treated, the nature and severity of the disease, the nature of the preparations and the route of administration of the drug and the period of time over which administration is performed. In some cases, it may be sufficient to use less than the above-stated quantity of active substance, while in other cases more than the above-stated quantity of active substance must be used. The person skilled in the art will use his/her skill to determine the optimum dosage and route of administration required in each particular case.

The compounds according to the invention may be given to animals in conventional concentrations and preparations together with feed or feed preparations or with drinking water.

The compounds according to the invention also show an excellent herbicidal activity.

A person skilled in the art knows the methods of preparation for example from U.S. Pat. No. 4,405,357.

The activity of the compounds is determined using a test system. This system is based upon in vitro measurement of growth of parasites, bacteria, viruses and fungi.

For example, antimalarial activity is determined by measuring the inhibition of the growth of malaria parasites in blood cultures. Antibacterial activity is determined on the basis of measuring the inhibition of bacterial growth onnutrient media and in liquid cultures. Antiviral activity is determined on the basis of the formation of viral elements in cell cultures.

Some of the micro-organisms which are to be investigated may be only investigated in animal models. In this case, the appropriate models will then be used.

Substances which exhibit activity in in vitro measurement systems are then further investigated in in vivo models. Antiparasitic, antiviral, fungicidal or antibacterial activity is further evaluated in the appropriate animal models.

Screening for herbicidal activity is determined by means of algal systems and measurement of isoprene emissions from plants under standard conditions.

The activity of some compounds according to the invention is described below with the help of examples:

EXAMPLES CONCERNING THE ACTIVITY

Experiments show that the action of the compounds is based on inhibition of the 1-deoxy-D-xylulose 5-phosphate (DOXP)metabolic pathway, which can be detected in micro-organisms and plants, but not for human beings. The following example accordingly shows the action of the compounds according to the invention on DOXP reductoisomerase.

Example 1

DOXP reductoisomerase of Escherichia coli was expressed as a recombinant protein in $E.coli$. The activity of DOXP reductoisomerase has been determined in a batch, which comprised 100 mM tris-HCl (pH=7,5), 1 mM $MnCl_2$, 0,3 mM NADPH and 1 mM DOXP. The oxidation of NADPH was measured here in a spectrophotometer at 365 mn. For carrying out the inhibition studies the activity of the DOXP reductoisomerase in presence of the compounds 1 to 8 listed on page 9 in various concentrations between 0,1 and 100 pmol $1^{-1}$ has been measured. The concentration at which the enzyme is inhibited to half the maximum extent ($IC_{50}$) was determined from the measurement values. The results, i.e. the $IC_{50}$-Werte are listed in table 1.

Example 2

The antimalaria activity of the compounds listed on page 9 was determined on in vitro cultures of the malaria pathogen Plasmodium falciparum. The depressions of a 96-well microtitre plate were charged with in each case 200 µl of an asynchroneous Plasmodium falciparum culture at a parasitaemia of 0,4% and haematokrit of 2%. A serial dilution series of the compounds in triple steps between concentrations of 100 to 0,14 µmol $1^{-1}$ was then prepared. The plates were incubated at 37° C., 3% $CO_2$ and 5% $O_2$ over a period of 48 hours. 30 µl medium supplemented with 27 µCi $ml^{-1}$ [$^3$H]-hypoxanthine were then added to each well. After incubation for 24 hours the parasites were harvested by filtration on a glass fibre filter and the radioactivity which had been incorporated was measured. The inhibition of the growth of parasites was measured as the percentage inhibition of the incorporation of tritium. Inhibition of the growth of the parasites has been determined as percentage inhibition of incorporation of tritium based on a comparison without the substance. The half-maximum inhibitory concentration (IC50) of the substance was determined by extrapolation of the values. The results, i.e. the IC50-Werte, are listed in table 1.

Example 3

The antibacterial activity of the compounds stated on page 9 was determined. The roman numerals refer to the particularly preferred compounds stated on pages to.

A dilution series comprising the concentrations 500, 100, 50, 10 and 0 µmol $1^{-1}$ of the individual compounds in LB medium is introduced into 5 culture microtubes in a volume of 0,5 ml. The tubes were inoculated with 10 µl of an overnight culture of $E.\ coli$ K12 and shaken overnight at 37° C. The growth of the bacteria was assessed on the basis of the turbidity of the medium. The minimum concentration causing inhibition of bacterial growth was determined (minimum inhibition concentration MIC)

The antibacterial activity of P. aeruginosa was determined in the same manner. The results are listed in table I.

TABLE I

| compound No. | IC50(nM) of DOXP reducto-isomerase from Helicobacter pilori |
|---|---|
| 1 | 22 |
| 2 | 110 |
| 3 | 125 |
| 4 | 78 |
| 5 | 100 |
| 6 | 130 |
| 7 | 18 |
| 8 | 24 |

TABLE I-continued

| compound No. | |
|---|---|
| | IC50(nM) of malaria culture (Plasmodium falciparum) |
| 1 | 800 |
| 2 | 1200 |
| 3 | 1700 |
| 4 | 9200 |
| 5 | 1200 |
| 6 | 1600 |
| 7 | 400 |
| 8 | 700 |
| | MIC(nM) of bacteria culture (Pseudomonas aeruginosa) |
| 1 | 500 |
| 2 | 1600 |
| 3 | 2200 |
| 4 | 7000 |
| 5 | 2200 |
| 6 | 2500 |
| 7 | 9000 |
| 8 | 7300 |

The hlerbicidal activity of the compounds according to the present invention is described below:

Example 4

The determination of herbicidal activity is performed according to standard procedure. Again the compounds listed on page 9 are tested.

Compound: 1

Hydro Vorauflauf

| Gramm/Hektar | Reis | Lepidium | Echinochloa | Solanum |
|---|---|---|---|---|
| 1000 | 50% | 40% | 80% | 0% |

Erde Vorauflauf

| Gramm/Hektar | Zea mays | Beta vulgaris | Alopecurus myosuroides | Avena fatua | Cyperus esculentus | Setaria viridis |
|---|---|---|---|---|---|---|
| 500 | 0% | 30% | 50% | 0% | 0% | 0% |

| Gramm/Hektar | Abutilon theophrasti | Amaranthus retroflexus | Galium aperine | Sinapis arvensis | Xanthium strumarium |
|---|---|---|---|---|---|
| 500 | 0% | 0% | 0% | 40% | 0% |

Erde Nachauflauf

| Gramm/Hektar | Zea mays | Beta vulgaris | Alopecurus myosuroides | Avena fatua | Cyperus esculentus | Setaria viridis |
|---|---|---|---|---|---|---|
| 500 | 80% | 70% | 50% | 50% | 0% | 95% |

| Gramm/Hektar | Abutilon theophrasti | Amaranthus retroflexus | Galium aperine | Sinapis arvensis | Xanthium strumarium |
|---|---|---|---|---|---|
| 500 | 40% | 0% | 90% | 95% | 60% |

Compound: 2

Hydro Vorauflauf

| Gramm/Hektar | Reis | Lepidium | Echinochloa | Solanum |
|---|---|---|---|---|
| 1000 | 0% | 0% | 0% | 0% |

Erde Vorauflauf

| Gramm/Hektar | Zea mays | Beta vulgaris | Alopecurus myosuroides | Avena fatua | Cyperus esculentus | Setaria viridis |
|---|---|---|---|---|---|---|
| 500 | 0% | 0% | 0% | 0% | 0% | 0% |

| Gramm/Hektar | Abutilon theophrasti | Amaranthus retroflexus | Galium aperine | Sinapis arvensis | Xanthium strumarium |
|---|---|---|---|---|---|
| 500 | 0% | 0% | 0% | 0% | 0% |

Erde Nachauflauf

| Gramm/Hektar | Zea mays | Beta vulgaris | Alopecurus myosuroides | Avena fatua | Cyperus esculentus | Setaria viridis |
|---|---|---|---|---|---|---|
| 500 | 0% | 0% | 0% | 30% | 0% | 90% |

| Gramm/Hektar | Abutilon theophrasti | Amaranthus retroflexus | Galium aperine | Sinapis arvensis | Xanthium strumarium |
|---|---|---|---|---|---|
| 500 | 0% | 0% | 0% | 30% | 50% |

Compound: 3

Hydro Vorauflauf

| Gramm/Hektar | Reis | Lepidium | Echinochloa | Solanum |
|---|---|---|---|---|
| 4000 | 40% | 30% | 40% | 0% |

Erde Vorauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 0% | 30% | 60% | 0% | 0% | 0% |

| Gramm/Hektar | Abutilon theophrasti | Amaranthus retroflexus | Galium aperine | Sinapis arvensis | Xanthium strumarium |
|---|---|---|---|---|---|
| 2000 | 0% | 0% | 0% | 30% | 0% |

Compound: 3

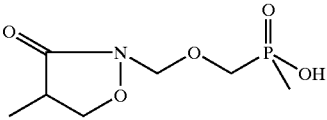

Erde Nachauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 70% | 90% | 60% | 50% | 0% | 70% |

| Gramm/Hektar | Abutilon theophrasti | Amaranthus retroflexus | Galium aperine | Sinapis arvensis | Xanthium strumarium |
|---|---|---|---|---|---|
| 2000 | 60% | 60% | 40% | 70% | 60% |

Compound: 4

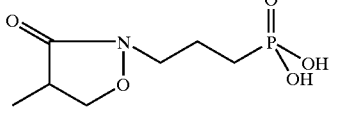

Hydro Vorauflauf

| Gramm/Hektar | Reis | Lepidium | Echinochloa | Solanum |
|---|---|---|---|---|
| 4000 | 30% | 30% | 70% | 30% |

Erde Vorauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 30% | 60% | 0% | 60% | 0% | 0% |

| Gramm/Hektar | Abutilon theophrasti | Amaranthus retroflexus | Galium aperine | Sinapis arvensis | Xanthium strumarium |
|---|---|---|---|---|---|
| 2000 | 0% | 0% | 0% | 70% | 0% |

Erde Nachauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 70% | 50% | 70% | 40% | 0% | 90% |

| Gramm/Hektar | Abutilon theophrasti | Amaranthus retroflexus | Galium aperine | Sinapis arvensis | Xanthium strumarium |
|---|---|---|---|---|---|
| 2000 | 50% | 40% | 70% | 60% | 90% |

Compound: 5

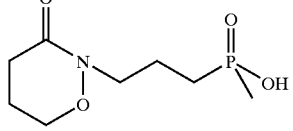

Hydro Vorauflauf

| Gramm/Hektar | Reis | Lepidium | Echinochloa | Solanum |
|---|---|---|---|---|
| 4000 | 40% | 40% | 60% | 0% |

Erde Vorauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 0% | 30% | 60% | 0% | 0% | 0% |

| Gramm/Hektar | Abutilon theophrasti | Amaranthus retroflexus | Galium aperine | Sinapis arvensis | Xanthium strumarium |
|---|---|---|---|---|---|
| 2000 | 0% | 0% | 0% | 50% | 0% |

Erde Nachauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 80% | 40% | 80% | 40% | 0% | 95% |

| Gramm/Hektar | Abutilon theophrasti | Amaranthus retroflexus | Galium aperine | Sinapis arvensis | Xanthium strumarium |
|---|---|---|---|---|---|
| 2000 | 40% | 30% | 70% | 90% | 60% |

Compound: 6

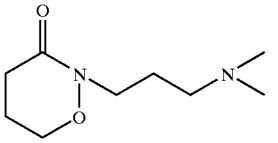

Hydro Vorauflauf

| Gramm/Hektar | Reis | Lepidium | Echinochloa | Solanum |
|---|---|---|---|---|
| 4000 | 40% | 30% | 50% | 0% |

Erde Vorauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 0% | 60% | 70% | 0% | 0% | 0% |

| Gramm/Hektar | Abutilon theophrasti | Amaranthus retroflexus | Galium aperine | Sinapis arvensis | Xanthium strumarium |
|---|---|---|---|---|---|
| 2000 | 0% | 0% | 0% | 30% | 0% |

Compound: 6

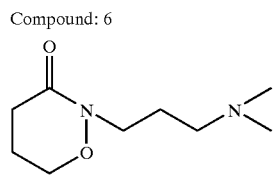

Erde Nachauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 70% | 40% | 40% | 60% | 0% | 70% |

| Gramm/Hektar | Abutilon theophrasti | Amaranthus retroflexus | Galium aperine | Sinapis arvensis | Xanthium strumarium |
|---|---|---|---|---|---|
| 2000 | 60% | 70% | 80% | 60% | 60% |

Compound: 7

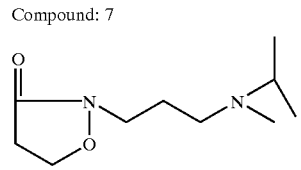

Hydro Vorauflauf

| Gramm/Hektar | Reis | Lepidium | Echinochloa | Solanum |
|---|---|---|---|---|
| 4000 | 30% | 0% | 40% | 30% |

Erde Vorauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 30% | 70% | 30% | 30% | 0% | 0% |

| Gramm/Hektar | Abutilon theophrasti | Amaranthus retroflexus | Galium aperine | Sinapis arvensis | Xanthium strumarium |
|---|---|---|---|---|---|
| 2000 | 0% | 20% | 0% | 30% | 0% |

Erde Nachauflauf

| Gramm/Hektar | Zea mays | Beta vulgaris | Alopecurus myosuroides | Avena fatua | Cyperus esculentus | Setaria viridis |
|---|---|---|---|---|---|---|
| 2000 | 70% | 70% | 80% | 80% | 0% | 90% |

| Gramm/Hektar | Abutilon theophrasti | Amaranthus retroflexus | Galium aperine | Sinapis arvensis | Xanthium strumarium |
|---|---|---|---|---|---|
| 2000 | 50% | 50% | 95% | 80% | 90% |

Compound: 8

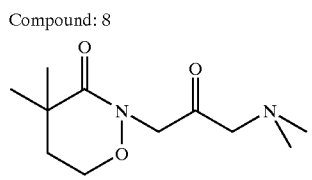

Hydro Vorauflauf

| Gramm/Hektar | Reis | Lepidium | Echinochloa | Solanum |
|---|---|---|---|---|
| 2000 | 0% | 30% | 40% | 30% |

Erde Vorauflauf

| Gramm/Hektar | Zea mays | Beta vulgaris | Alopecurus myosuroides | Avena fatua | Cyperus esculentus | Setaria viridis |
|---|---|---|---|---|---|---|
| 1000 | 30% | 30% | 30% | 30% | 0% | 0% |

| Gramm/Hektar | Abutilon theophrasti | Amaranthus retroflexus | Galium aperine | Sinapis arvensis | Xanthium strumarium |
|---|---|---|---|---|---|
| 1000 | 0% | 20% | 0% | 30% | 0% |

Erde Nachauflauf

| Gramm/Hektar | Zea mays | Beta vulgaris | Alopecurus myosuroides | Avena fatua | Cyperus esculentus | Setaria viridis |
|---|---|---|---|---|---|---|
| 1000 | 70% | 40% | 70% | 80% | 0% | 90% |

| Gramm/Hektar | Abutilon theophrasti | Amaranthus retroflexus | Galium aperine | Sinapis arvensis | Xanthium strumarium |
|---|---|---|---|---|---|
| 1000 | 50% | 50% | 70% | 90% | 90% |

What is claimed is:

1. A method for the treatment of infectious diseases caused by bacteria, fungi or parasites comprising:
    administering to a patient having an infection caused by said bacteria, fungi or parasites a therapeutically effective amount of a compound of formula (I)

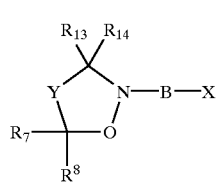

(I)

wherein Y is a $C_{1-3}$-alkylene group, which is substituted by the substituents $R_1$ and $R_2$ and optionally by the substituents $R_3$ to $R_6$, wherein $R_1$ to $R_8$ are the same or different and are selected from the group consisting of hydrogen, hydroxy, halogen, substituted and unsubstituted alkyl groups, substituted and unsubstituted cycloalkyl-($C_{0-26}$)-alkyl groups, substituted and unsubstituted cycloalkoxy-($C_{0-26}$-alkyl groups, substituted and unsubstituted alkoxy ($C_{0-26}$)-alkyl groups, substituted and unsubstituted amino groups and substituted, unsubstituted thio($C_{0-26}$)-alkyl groups, substituted and unsubstituted sulfonyl($C_{0-26}$)-alkyl groups, substituted and unsubstituted sulfinyl($C_{0-26}$)-alkyl groups and substituted or unsubstituted acyl radicals, wherein each alkyl radical, each alkoxy radical and each acyl radical branched or unbranched and each alkyl radical, each alkoxy radical and each cycloalkyl group is saturated or unsaturated having one or more double or triple bonds and one or two carbon atoms of the cycloalkyl groups may be replaced by nitrogen, oxygen or sulphur atoms, and $R_{13}$ and $R_{14}$ are defined like $R_1$ to $R_9$ or together form an oxo group, wherein X represents the organo phosphorous group,

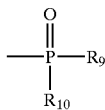

wherein $R_9$ and $R_{10}$ are the same or different and are selected from the group consisting of hydrogen, substituted and unsubstituted ($C_{1-26}$)-alkyl groups, substituted and unsubstituted hydroxy-($C_{1-26}$)-alkyl groups, substituted and unsubstituted cycloalkyl-($C_{0-26}$)-alkyl groups, substituted and unsubstituted acyl, halogen, $OX_9$ and $OX_{10}$, wherein each alkyl radical, each alkoxy radical and each acyl radical branched or unbranched and each alkyl radical, each alkoxy radical and each cycloalkyl group is saturated or unsaturated having one or moore double or triple bonds and one or two carbon atoms of the cycloalkyl groups may be replaced by nitrogen, oxygen or sulphur atoms, wherein $X_9$ or $X_{10}$ may be identical or different and are selected from the group consisting of hydrogen, substituted and unsubstituted ($C_{1-26}$)-alkyl groups, substituted and unsubstituted hydroxy-($C_{1-26}$)-alkyl groups, substituted and unsubstituted cycloalkyl-($C_{0-26}$)-alkyl groups, substituted and unsubstituted acyl silyl, a cation of an organic and inorganic base, a metal of main group I, II or m of the periodic system, ammonium, substituted ammonium and ammonium compounds which are derived from ethylenediamine or amino acids, wherein each alkyl radical, each alkoxy radical and each acyl radical branched or unbranched and each alkyl radical, each alkoxy radical and each cycloalkyl group saturated or unsaturated having one or more double bonds or triple bonds and one or two carbon atoms of the cycloalkyl groups may be replaced by nitrogen, oxygen or sulphur atoms, or wherein X represents the amino group

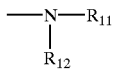

wherein $R_{11}$ and $R_{12}$ are the same or different and are selected from the group consisting of hydrogen, substituted and unsubstituted alkyl groups, substituted and unsubstituted cycloalkyl-($C_{0-26}$)-alkyl groups, substituted and unsubstituted cycloalkoxy-($C_{0-26}$)-alkyl groups, substituted and unsubstituted alkoxy ($C_{0-26}$)-alkyl groups, and wherein each alkyl radical, each alkoxy radical and each alkyl radical, each alkoxy radical and each cycloalkyl group is saturated or unsaturated with one or more double bonds or triple bonds and one or two carbon atoms of the cycloalkyl groups may be replaced by nitrogen, oxygen or sulphur atoms, wherein B is selected from the group consisting of substituted and unsubstituted $C_{1-26}$-alkylene groups, wherein one C-atom may be replaced by an oxygen atom and one C-atom may be replaced by a sulphur atom or two C-atomns may be replaced by a S-heterocycle and wherein each alkylene radical may be branched or unbranched and is saturated or unsaturated having one or more double bonds or triple bonds and may be substituted with one or more hydroxy groups, halogen groups or oxo groups, or pharnaceutically acceptable salts, esters and salts of the esters for the inhibition of the 1-deoxy-D-xylulose-5-phosphate(DOXP)-metabolic pathway.

2. The method according to claim 1, wherein $R_{13}$ and $R_{14}$ together form an oxo group in $\alpha$-position to the nitrogen atom.

3. The method according to claim 1, wherein Y represents a methylene group.

4. The method according to claim 3, wherein said methylene group is substituted with two methyl groups.

5. The method according to claim 1 wherein B represents ether group (II)

wherein $A_1$ is absent or is a ($C_{1-9}$)-alkylene radical, and $A_2$ is absent or is selected from the group consisting of ($C_{1-9}$)-alkylene radicals, a sulphur atom and a ($C_{3-8}$)-heterocycle, which comprises at least one sulphur atom.

6. The method according to claim 5, wherein $A_1$ and $A_2$ each represent a methylene group.

7. The method according to claim 1, wherein B represents keto group (III)

wherein $A_3$ and $A_4$, out of which one or both may be absent, are the same or different, are selected from the group consisting of ($C_{1-9}$)-alkylene radicals, wherein all the ($C_{1-9}$)-alkylene radicals are branched or unbranched, may comprise one or more double bonds or may be substituted with a hydroxyl group or a halogen group.

8. The method according to claim 7, wherein $A_3$ is absent and $A_4$ is a methylene group or an ethylene group.

9. The method according to claim 1, wherein B is a 2-hydroxypropylene group.

10. The method according to claim 1, wherein the compound is selected from the group, consisting of

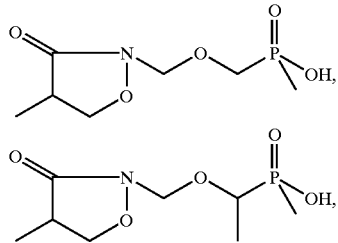

-continued
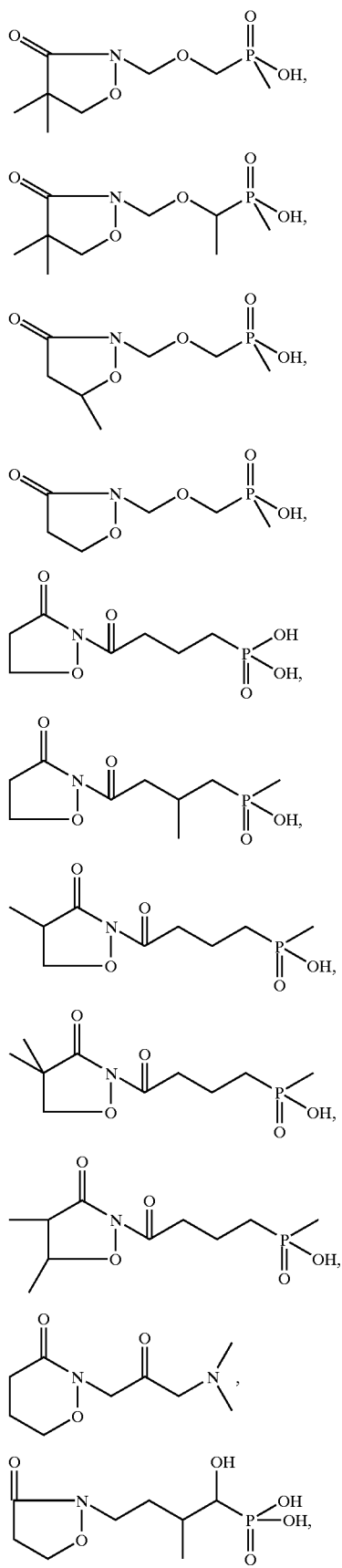
-continued
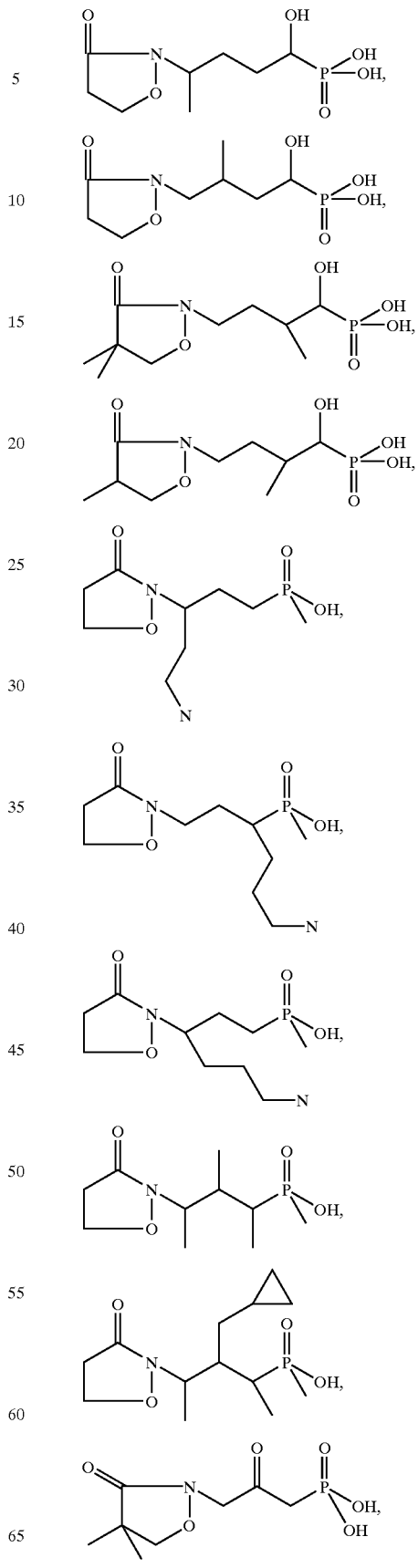

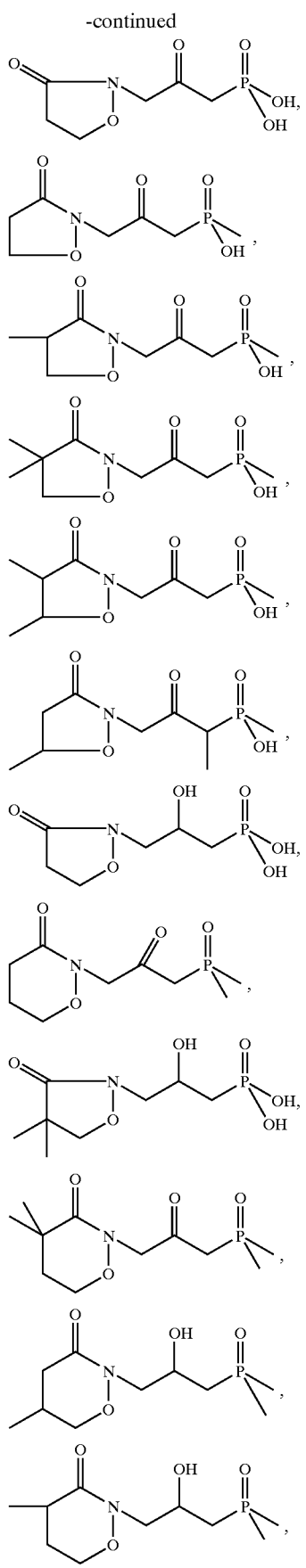
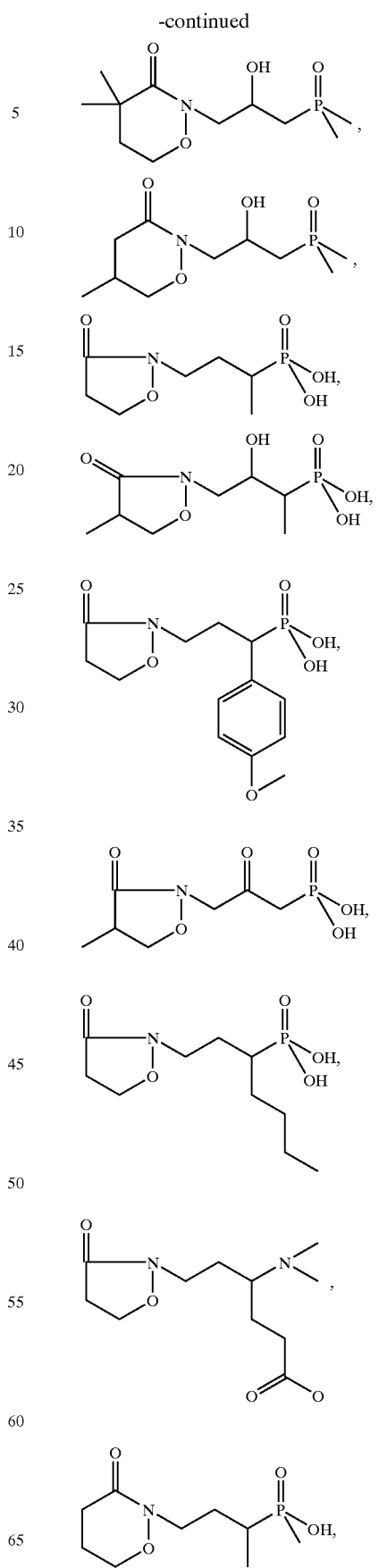

-continued
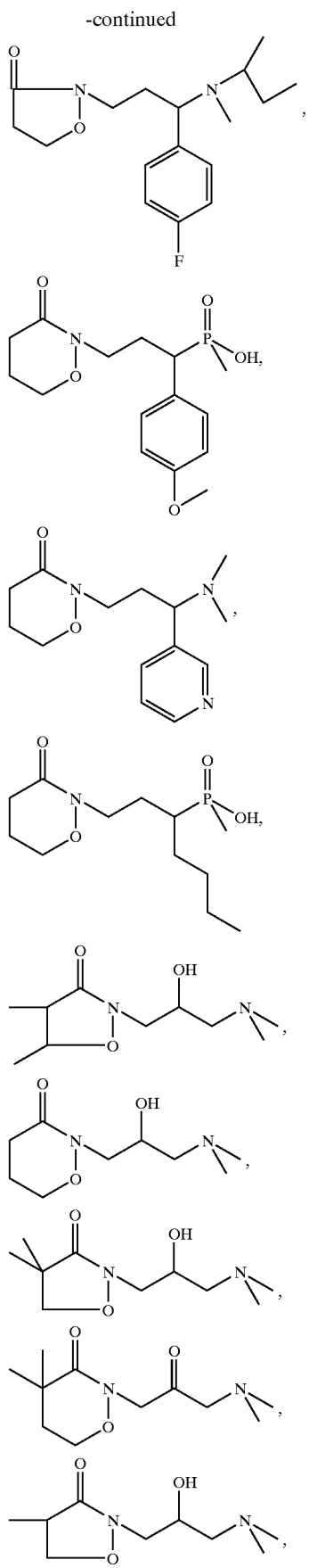
-continued
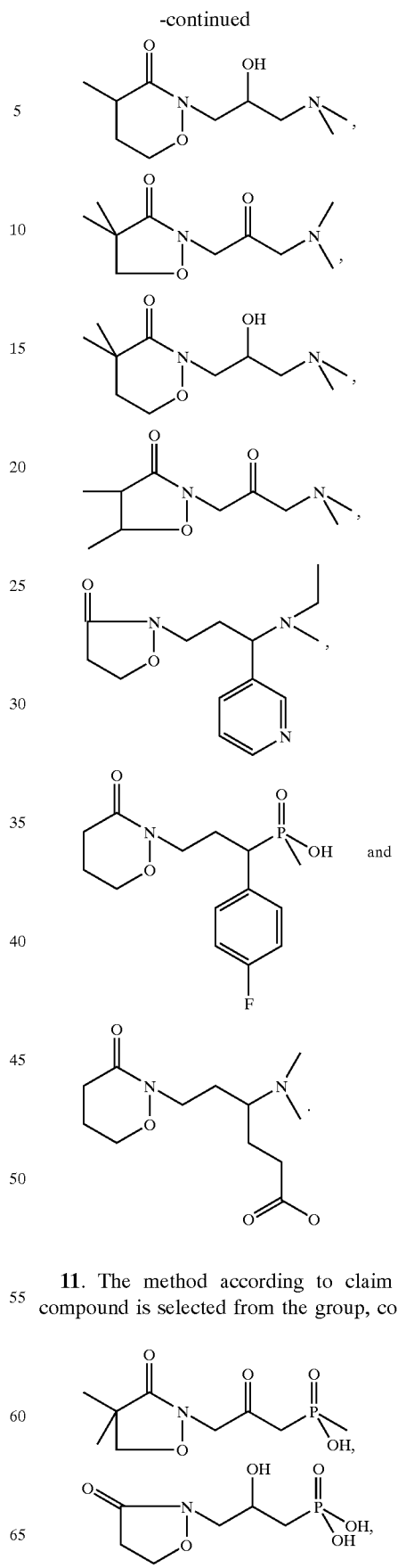
11. The method according to claim 10, wherein the compound is selected from the group, consisting of
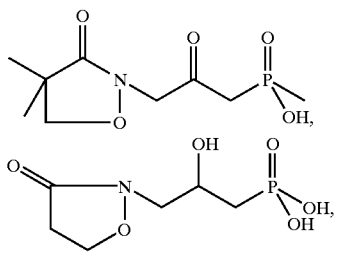

-continued
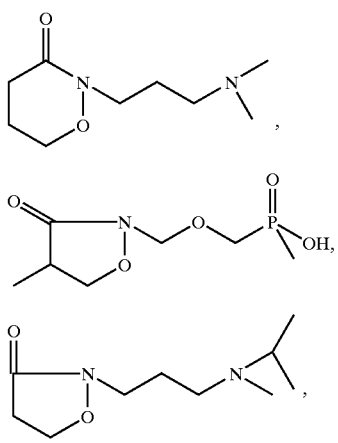
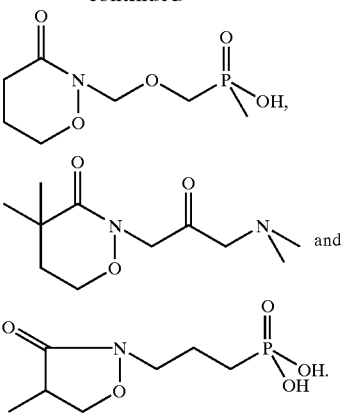
* * * * *